US011278546B2

(12) United States Patent
Tang-Liu et al.

(10) Patent No.: US 11,278,546 B2
(45) Date of Patent: Mar. 22, 2022

(54) MULTIKINASE INHIBITORS AND USES IN OCULAR FIBROSIS

(71) Applicant: AIVIVA BIOPHARMA, INC., Las Vegas, NV (US)

(72) Inventors: Diane Tang-Liu, Las Vegas, NV (US); Gerald Woodrow Devries, San Clemente, CA (US); Tiffany Constance Liu, Las Vegas, CA (US)

(73) Assignee: AIVIVA BIOPHARMA, INC., Las Vegas, NV (US)

( * ) Notice: Subject to any disclaimer, the term of this patent is extended or adjusted under 35 U.S.C. 154(b) by 180 days.

(21) Appl. No.: 16/319,265

(22) PCT Filed: Jul. 21, 2017

(86) PCT No.: PCT/US2017/043186
§ 371 (c)(1),
(2) Date: Jan. 18, 2019

(87) PCT Pub. No.: WO2018/022437
PCT Pub. Date: Feb. 1, 2018

(65) Prior Publication Data
US 2019/0275034 A1    Sep. 12, 2019

Related U.S. Application Data

(60) Provisional application No. 62/492,936, filed on May 1, 2017, provisional application No. 62/365,429, filed on Jul. 22, 2016.

(51) Int. Cl.
| | | |
|---|---|---|
| *A61P 27/02* | (2006.01) | |
| *A61K 9/00* | (2006.01) | |
| *A61K 31/47* | (2006.01) | |
| *A61K 31/496* | (2006.01) | |
| *A61K 31/438* | (2006.01) | |

(52) U.S. Cl.
CPC .......... *A61K 31/496* (2013.01); *A61K 9/0048* (2013.01); *A61K 31/438* (2013.01); *A61K 31/47* (2013.01); *A61P 27/02* (2018.01)

(58) Field of Classification Search
CPC .................................................. A61K 31/47
See application file for complete search history.

(56) References Cited

U.S. PATENT DOCUMENTS

| | | | |
|---|---|---|---|
| 5,767,079 A | 6/1998 | Glaser et al. | |
| 7,306,799 B2* | 12/2007 | Wiegand | C07K 14/71 424/134.1 |
| 9,636,332 B2 | 5/2017 | Zarnitsyn et al. | |
| 2008/0213274 A1* | 9/2008 | Sabbadini | C07K 16/18 424/141.1 |
| 2008/0241252 A1* | 10/2008 | Lyons | A61P 27/02 424/489 |
| 2009/0203693 A1* | 8/2009 | Yokohama | A61K 31/4545 514/235.2 |
| 2010/0111898 A1* | 5/2010 | Pelura | A61K 38/1716 424/85.2 |
| 2015/0031723 A1* | 1/2015 | Cao | A61K 45/06 514/313 |
| 2015/0258120 A1 | 9/2015 | Zarnitsyn et al. | |
| 2015/0366866 A1 | 12/2015 | Ali et al. | |
| 2016/0206628 A1 | 7/2016 | Zarnitsyn et al. | |
| 2016/0317438 A1* | 11/2016 | Ashton | A61K 9/0051 |

FOREIGN PATENT DOCUMENTS

| | | | |
|---|---|---|---|
| CA | 3026118 A1 | 12/2017 | |
| JP | 2015535293 A | 12/2015 | |
| WO | 2013126799 A1 | 8/2013 | |
| WO | WO-2014074823 A1 * | 5/2014 | ............. A61K 45/06 |
| WO | 2016-200688 A1 | 12/2016 | |
| WO | 2016209555 A1 | 12/2016 | |
| WO | 2017015591 A1 | 1/2017 | |
| WO | 2017062694 A1 | 4/2017 | |
| WO | 2017210130 A1 | 12/2017 | |
| WO | 2017210132 A1 | 12/2017 | |
| WO | 2018054077 A1 | 3/2018 | |

OTHER PUBLICATIONS

Matsui et al., Clinical Cancer Research vol. 14 pp. 5459-5465. Published 2008 (Year: 2008).*
Zhong, Hua et al., "Evaluation of Pirfenidone as a New Postoperative Antiscarring Agent in Experimental Glaucoma Surgery", Invest Ophthalmol Vis Scie, 52: 3136-3142, 2011.
Amparo, Francisco et al., "Safety and Efficacy of the Multitargeted Receptor Kinase Inhibitor Pazopanib in the Treatment of Corneal Neovascularization", Investigative Opthalmology & Visual Science, Jan. 2013, vol. 54, No. 1, pp. 537-544 (http://iovs.arvojournals.org/pdfaccess.ashx?url=/data/journals/iovs/933466/ on Dec. 15, 2017).
Daniel, Ebenezer et al., "Risk of Scar in the Comparison of Age-related Macular Degeneration Treatments Trials", Ophthalmology, Mar. 2014: 121(3): 656-666.

(Continued)

*Primary Examiner* — Theodore R. Howell
*Assistant Examiner* — George W Kosturko
(74) *Attorney, Agent, or Firm* — Maschoff Brennan; Brent A. Johnson; David Old

(57) ABSTRACT

A method for preventing and/or treating fibrosis associated with an eye-related disease or disorder includes administering an effective amount of a multikinase inhibitor to a subject in need thereof. The multikinase inhibitor is nintedanib, lenvatinib, a combination thereof, or a salt thereof. The eye-related disease or disorder is corneal transparency, corneal scar formation, secondary cataract formation, glaucoma filtration surgery, ocular surgical procedures and implants, photorefractive keratectomy, laser in situ keratomileusis, formation and contraction of pre- and epiretinal membranes, proliferative vitreoretinopathy, subretinal fibrosis/scarring, retinal gliosis, or formation of choroidal membranes.

18 Claims, 4 Drawing Sheets

(56) References Cited

OTHER PUBLICATIONS

Friedlander, Martin, "Fibrosis and Diseases of the Eye", J. Clin Invest, Mar. 1, 2007; 117(3): 576-586.
Grimminger, Friedrich et al., "The role of tyrosine kinases in the pathogenesis of idiopathic pulmunary fibrosis", Eur Respir J., 2015; 45: 1426-1433.
International Search Report & Written Opinion, PCT/US2017/043186, dated Jan. 11, 2018.
Kudelka, Matthew R. et al., "Emergence of dual VEGF and PDGF antagonists in the treatment of exudative age-related macular degeneration", Expert Rev Ophthalmol, 2013: 8(5): 475-484.
Maguire, Maureen G, "5-Year Outcomes with Anti-VEGF Treatment of Neovascular Age-related Macular Degeneration (AMD): The Comparison of AMD Treatments Trials", Ophthalmology, Aug. 2016; 123(8): 1751-1761.
Richeldi, Luca et al., "Idiopathic pulmunary fibrosis", The Lancet, Published online Mar. 29, 2017; http://dx.doi.org/10.1016/S0140-6736(17)30866-8.
Yu-Wai-Man, Cynthia et al., "Developing novel anti-fibrotic therapeutics to modulate post-surgical wound healing in glaucoma: big potential for small molecules", Expert Review of Ophthalmology, 2015, vol. 10, Issue 1, pp. 65-76.
Huu, V.A.N et al., Light-responsive nanoparticle depot to control release of a small molecule angiogenesis inhibitor in the posterior segment of the eye, Journal of Controlled Release, 200, 71-77, bearing an alleged date of Feb. 2015.
Extended European Search Report for European Patent Application No. 17835012.0, dated Dec. 15, 2020.
Chaudhary, N.I. et al., Inhibition of PDGF, VEGF and FGF signalling attenuates fibrosis, European Respiratory Journal, 29(5), 976-985, May 2007.
Eren, K. et al., The Suppression of Wound Healing Response with Sirolimus and Sunitinib Following Experimental Trabeculectomy in a Rabbit Model, Current Eye Research, 41(3), 367-376, Mar. 2016.
Huang, J. et al., Nintedanib Ameliorates Fibrotic and Vascular Manifestations in Preclinical Models of Systemic Sclerosis, Abstract No. 2153 Arthritis & Rheumatology, 67, 2584-2585, Oct. 2015.
Ishikawa, K. et al., Molecular mechanisms of subretinal fibrosis in age-related macular degeneration, Experimental Eye Research, 142, 19-25, Jan. 2016.

* cited by examiner

Fig. 1 Total Corneal Vessel Area (mm$^2$)
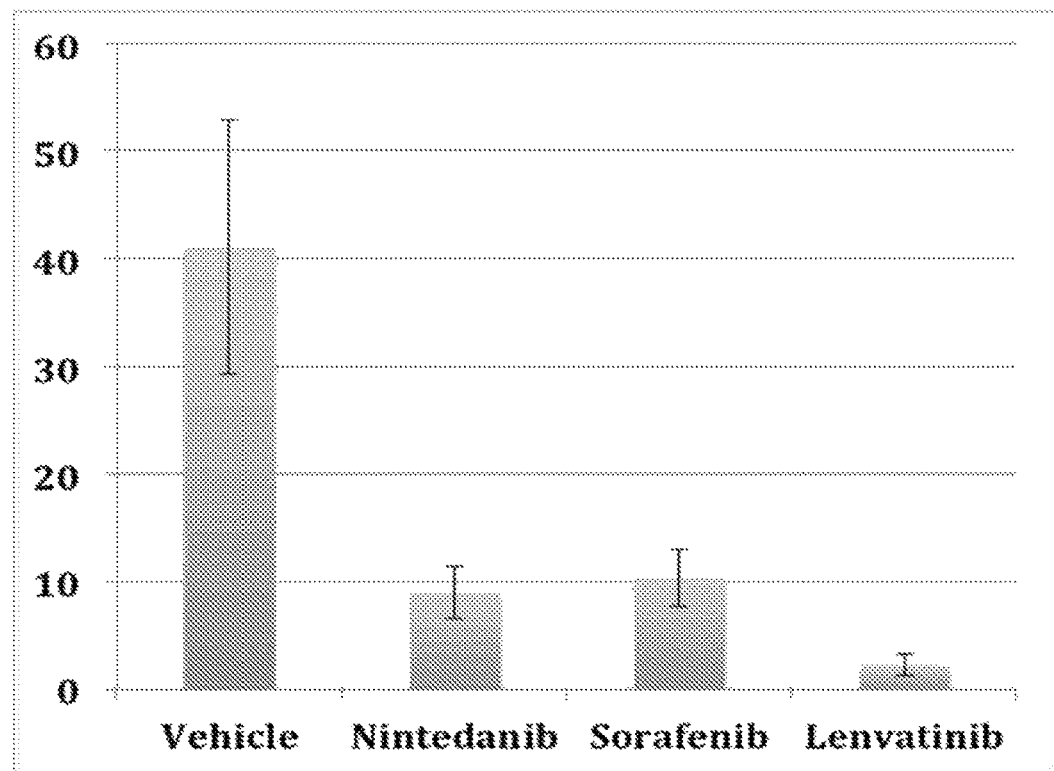
Fig. 2 Histological Findings Corneal Suture Fibrosis Model
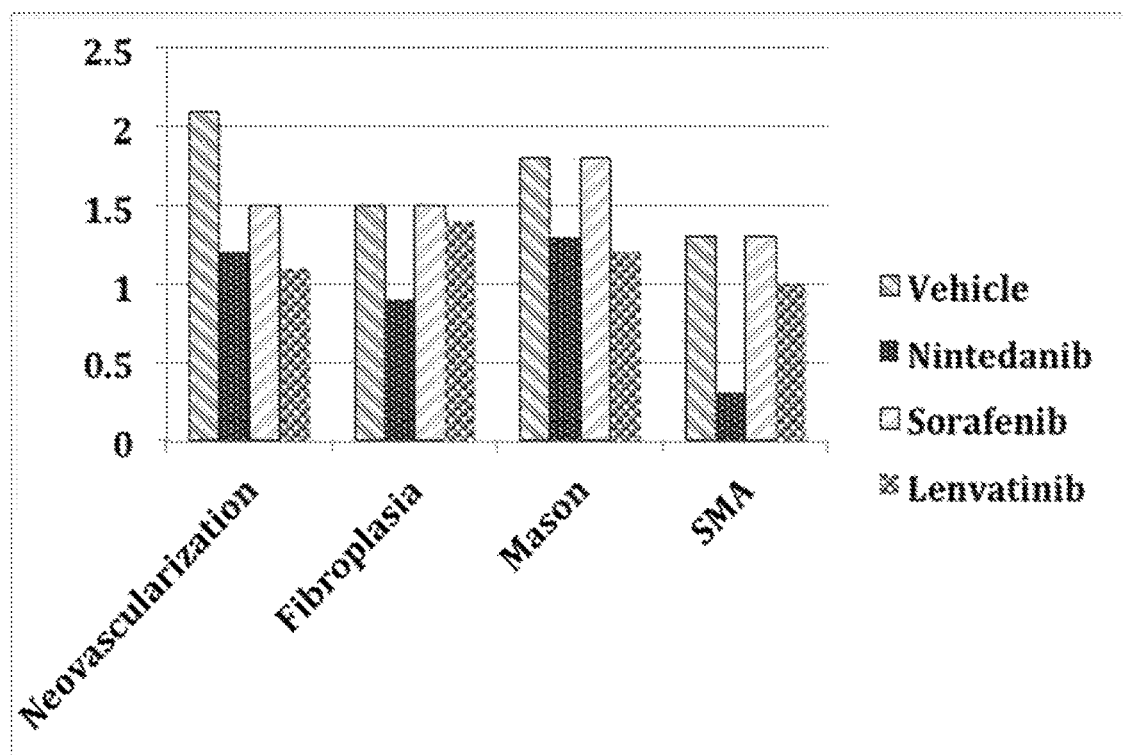

Fig. 3 A representative bleb treated with sorafenib on Day 4.
Figure 4. Treatment Effect on Bleb Survival for 30 Days after Glaucoma Filtration Surgery in Rabbits.
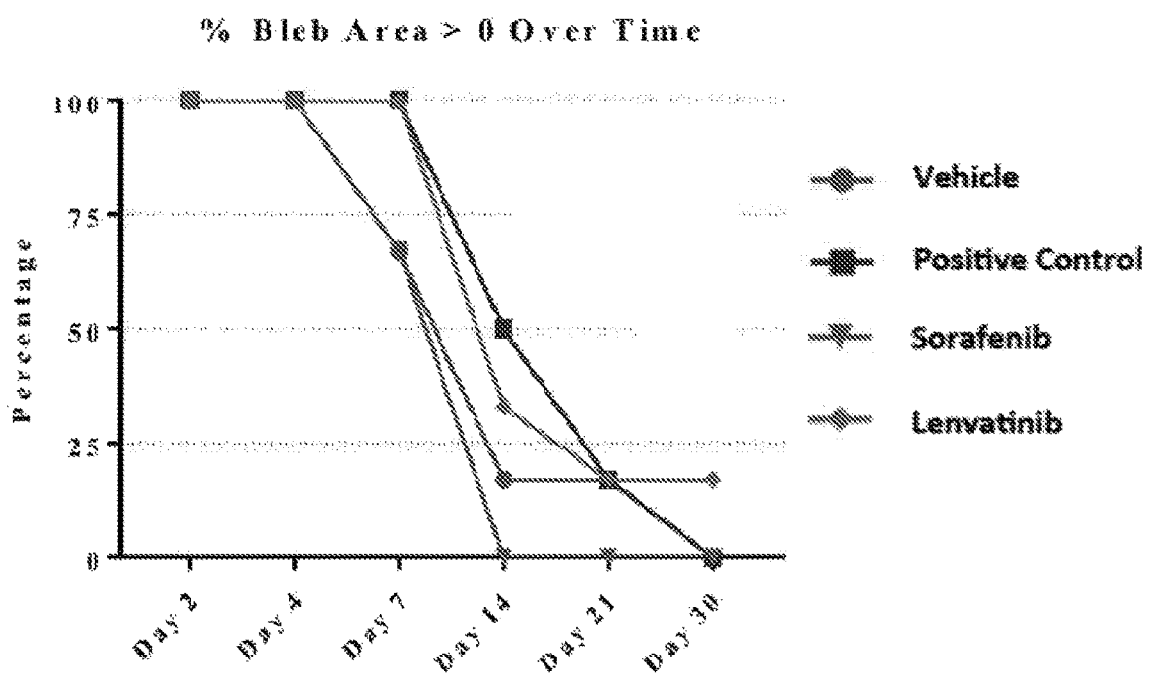

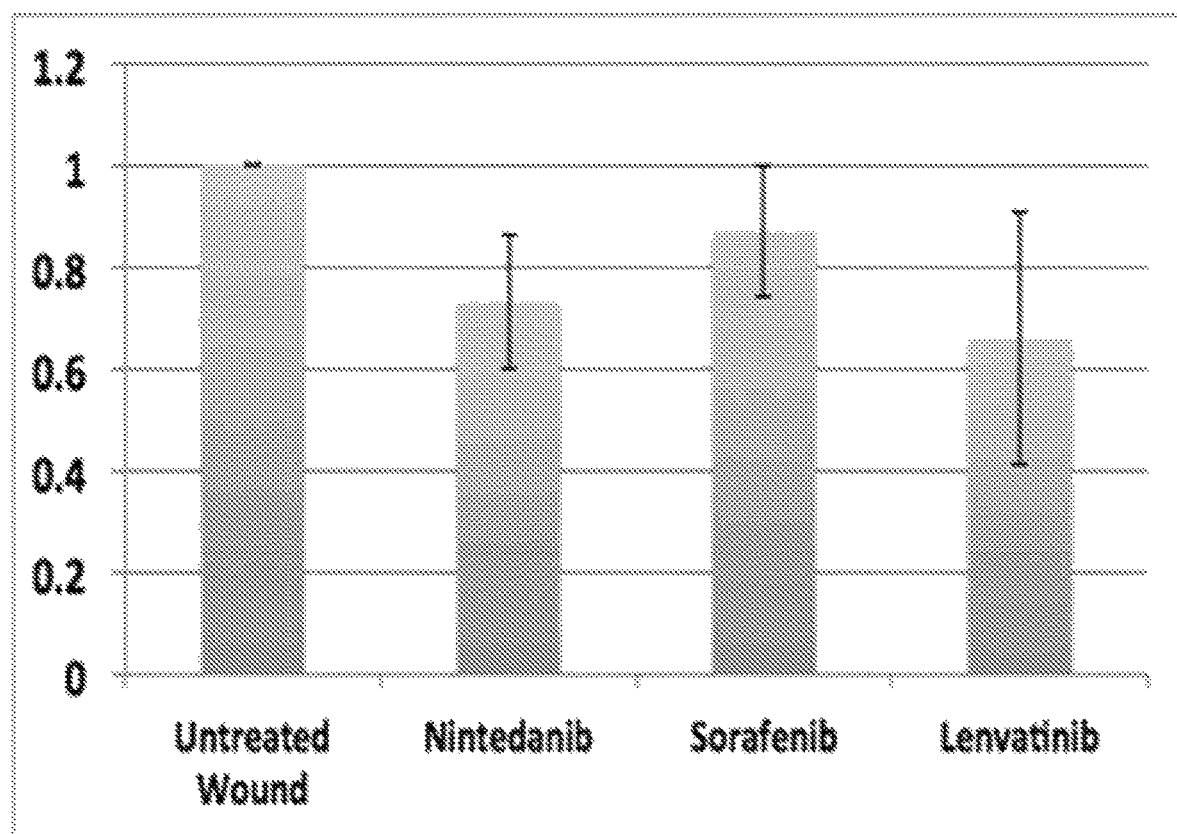
Fig. 5 TGF beta1 mRNA Expression in Rabbit Dermal Wound Model

Fig. 6 Representative images of two weeks post laser in mice.
A. Fluorescein fundus angiography.
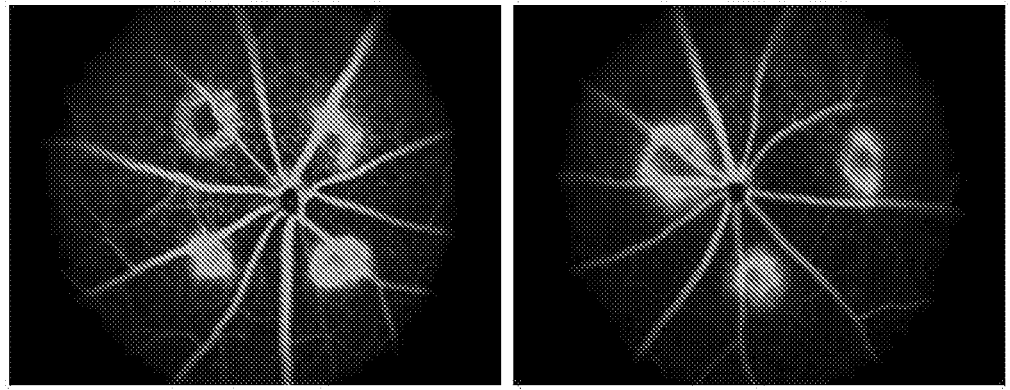
B. Isolectin B4
C. Isolectin B4/DAPI
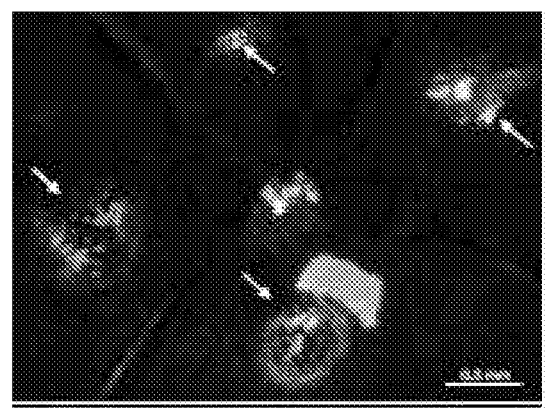

MULTIKINASE INHIBITORS AND USES IN OCULAR FIBROSIS

CROSS REFERENCE TO RELATED APPLICATIONS

This claims the priorities of U.S. Provisional Patent Applications Nos. 62/492,936 filed on May 1, 2017 and 62/365,429, filed on Jul. 22, 2016.

FIELD OF INVENTION

The invention relates to compounds that possess a certain spectrum of multikinase inhibition activities. These multikinase inhibitors act on specific growth factors, cytokine signaling pathways, and/or phases of fibrotic responses. This invention also relates to methods of prevention and/or treatment of ocular fibrosis associated with disease states, disorders and/or surgical procedures, including corneal scarring, and fibrosis resulting from glaucoma filtration surgery and procedures, ocular procedures, age-related macular degeneration, and proliferative vitreoretinopathy.

BACKGROUND OF THE INVENTION

Ocular fibrosis leads to significant visual impairment and blindness in millions of people throughout the world (Friedlander M, J. Clin. Invest. 117: 576-586, 2007; Yu-Wai-Man C and Tee Khaw P, Expert Rev. Ophthalmol. 10: 65-76, 2014). It is involved in the pathogenesis, or failure of treatment, of all the major blinding diseases. Fibrosis is the formation of excess extracellular matrix in an organ or tissue as the result of a reparative or reactive process. The complexity of these responses has resulted in significant challenges in developing anti-fibrotic therapeutics and, therefore, a huge unmet medical need in this patient population.

In these disease states, there are a myriad of endogenous factors regulating cell proliferation, cell migration and transformation, and extracellular matrix deposition and remodeling. These factors include FGF, VEGF, PDGF, etc. Each of these factors has served as targets for the prevention and/or treatment of ocular disease. For example, inhibition of a single growth factor signaling pathway, e.g. VEGF, has led to improvement in patients with ocular diseases, such as age-related macular degeneration and diabetic retinopathy. However, targeting one factor alone has not resulted in satisfactory long-term outcomes (Ebenezer D et al., Ophthalmology 121: 656-666, 2014; Maguire M G et al., Ophthalmology 123: 1751-1761, 2016).

Inhibition of multiple growth factor signaling pathways at various stages in the fibrotic response may be a significantly better strategy. The use of multikinase inhibitors may lead to improved long-term outcomes. However, several multikinase inhibitors and/or combination treatments have not shown efficacy in fibrosis diseases, including macular degenerative diseases (Kudelka M et al., Expert Rev Ophthalmol. 8: 475-484, 2013) and idiopathic pulmonary fibrosis (Grimminger F et al., Eur. Respir. J. ERJ Express, Mar. 5, 2015; Richeldi L et al., The Lancet, Mar. 29, 2017).

While prior art kinase inhibitors show some success in treating some ocular diseases, there is still a need for therapeutic agents for treating ocular fibrosis.

SUMMARY OF THE INVENTION

Embodiments of the invention provide agents that possess a certain spectrum of multikinase inhibitor activities. These multikinase inhibitors are useful in the treatment of ocular fibrosis, which may be associated with disease states, disorders and/or surgical procedures in animals and humans. Embodiments of the invention are also directed to the therapeutic or prophylactic uses of such compounds or compositions, and to methods for treating ocular fibrosis, which may be associated with disease states, disorders and surgical procedures.

In one aspect, the invention provides a method for treating and/or preventing ocular fibrosis by administering a therapeutically effective amount of a multikinase inhibitor to a human subject or animal in need of such treatment or prevention, wherein the multikinase inhibitor may include, but not limited to, nintedanib and/or lenvatinib.

Embodiments of the invention relate to preventing and/or treating disease states, disorders and surgical procedures associated with fibrosis.

The invention has particular reference to preventing or treating the formation of ocular fibrosis associated diseases in humans and animals.

In accordance with embodiments of the invention, a method of the invention involves administering a multikinase inhibitor for treating or preventing disease states, disorders and surgical procedures associated with fibrosis, wherein the multikinase inhibitors include, but are not limited to nintedanib and/or lenvatinib.

In accordance with some embodiments of the invention, compounds/molecules of the present invention may be administered by parenteral, intramuscular, subcutaneous, ocular, topical, intraocular, intravitreal, intra-lesional, sub-conjunctival and sub-tenon injection, and drug delivery via eye-drops, spray, adhesive, and implants, and intra-canalicular delivery, to treat disease.

Liquid form compositions include, but are not limited to, solutions, suspensions, and emulsions. Sterile water or water-propylene glycol solutions of the active compounds/molecules are examples of liquid preparations suitable for administration.

The targets can be treated with the above-described methods for eye related diseases/disorders and ocular repair/wound healing associated with compromised corneal transparency, corneal scar formation, secondary cataract formation, glaucoma filtration surgery, ocular surgical procedures and implants, photorefractive keratectomy, laser in situ keratomileusis, formation and contraction of pre- and epiretinal membranes, proliferative vitreoretinopathy, proliferative diabetic retinopathy, diabetic macular edema, sub-retinal fibrosis/scarring, retinal gliosis, and formation of choroidal membranes, age-related macular degeneration, and retinal vein occlusion.

BRIEF DESCRIPTION OF THE DRAWINGS

FIG. 1 shows inhibition of corneal neovascularization in a rabbit corneal suture model by nintedanib, sorafenib, and lenvatinib in accordance with embodiments of the invention.

FIG. 2 shows inhibition of fibroplasia, collagen density, and alpha SMA (smooth muscle actin) in a rabbit corneal suture-induced fibrosis model by nintedanib and lenvatinib, but not by sorafenib.

FIG. 3 shows a representative conjunctival bleb formation in a rabbit model of glaucoma filtration surgery.

FIG. 4 shows treatment effect of multikinase inhibitors on bleb survival in a rabbit model of glaucoma filtration surgery.

FIG. 5 shows the effect of multikinase inhibitors on TGF beta1 mRNA expression in a rabbit dermal wound model.

FIG. 6 shows representative images of eyes two weeks post laser treatment. (A) Fluorescein fundus angiography; (B) Isolectin B4; and (C) Isolectin B4/DAPI.

DETAILED DESCRIPTION

Embodiments of the invention relate to preventing and/or treating fibrosis occurring in eyes (i.e., ocular fibrosis). Such fibrosis may be associated with various eye diseases or disorders. Such disorders include those resulting from undesired outcomes of surgical procedures. In accordance with embodiments of the invention, a method for treating ocular fibrosis, which may be associated with an eye disease or disorder, may involve giving to a subject in need of such treatments a composition comprising a multikinase inhibitor that has a select spectrum of activities to inhibit select kinases, such as VEGF and TGF beta.

A composition of the invention may comprise a multikinase inhibitor or a pharmaceutically acceptable salt thereof. As used herein, the term "multikinase inhibitor" refers to an inhibitor that can inhibit multiple kinases. As used herein, the term "pharmaceutically acceptable salts" refer to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compounds/molecules formed, for example, from non-toxic inorganic or organic acids. For example, such conventional non-toxic salts may include those derived from inorganic acids such as hydrochloric acid.

In accordance with some embodiments, the present invention also includes pharmaceutical compositions which contain, as the active ingredient, one or more of the compounds/molecules of the invention herein together with at least one pharmaceutically acceptable carrier, diluent or excipient.

In some embodiments, compounds/molecules of the present invention may be administered by parenteral, intramuscular, subcutaneous, ocular, topical, intraocular, intravitreal, intra-lesional, subconjunctival and sub-tenon injection routes.

The dosage will depend on the route of administration, the severity of the disease, age and weight of the patient and other factors normally considered by the attending physician, when determining the individual regimen and dosage level as the most appropriate for a particular patient. That is, a therapeutic effective amount would be based on the patient (age, sex, weight, etc.), the disease conditions, the route of administration, etc. One skilled in the art would be able to determine a therapeutically effective dose without inventive efforts.

In accordance with embodiments of the invention, the administration regimen could be before (induction) surgery, post-surgery (at or before trauma/acute inflammation, proliferation, remodeling, through maturation).

In accordance with embodiments of the invention, for preparing pharmaceutical compositions from the compounds/molecules of this invention, inert, pharmaceutically acceptable carriers can be either solid or liquid.

The term composition is intended to include the formulation of the active component or a pharmaceutically acceptable salt with a pharmaceutically acceptable carrier, diluent, or excipient.

Liquid form compositions include solutions, suspensions, and emulsions. Sterile water or water-propylene glycol solutions of the active compounds/molecular may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methylcellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations.

Compositions may be formulated for any suitable route and means of administration. Pharmaceutically acceptable carriers or diluents include those used in formulations suitable for parenteral administration. The formulations may conveniently be presented in unit dosage form and may be prepared by any of the methods well known in the art of pharmacy.

Embodiments of the invention will be illustrated with the following examples. One skilled in the art would appreciate that these examples are for illustration only and that other modifications and variations are possible without departing from the scope of the invention.

Example 1

In order to investigate the anti-fibrotic effect of test compounds following wounding in the eye, a suture-induced ocular fibrosis model was used. Suture was placed instromally under a microscope in the cornea of rabbits. In each eye, one 9-0 silk suture was placed, in a vertical position, temporal to the corneal center and a second suture was placed nasal to the corneal center. Each suture had two stromal incursions approximately 2 mm from the limbus. Test compounds having certain spectrum of multikinase inhibition activities and/or vehicle were topically instilled (35 μL/eye) in the eyes three times daily for 10 days starting from the day following surgery. The treatment groups include vehicle (as a control), nintedanib (0.3%, w/w), pirfenidone (1%, w/w), riociguat (0.3%, w/w), sorafenib (0.3%, w/w) and lenvatinib (0.3%, w/w). Six left eyes were used per treatment group.

During the in-life phase, gross ocular observations of very slight to moderate conjunctival congestion and swelling were similar among groups (including the control group), with the exception of the riociguat-treatment group, which tended to have a slightly more severe reaction over the course of the 10-day observation period. The animals were sacrificed on Day 11 and the eyes enucleated and dissected for histopathological evaluation.

The results show that lenvatinib, nintedanib, and sorafenib were efficacious in reducing the areas of neovascularization on the corneal surface (FIG. 1). In addition, nintedanib and lenvatinib significantly reduced fibroplasia and/or collagen density as evidenced by histological staining, including H&E and Masson's trichrome protocol used to differentiate cells from surrounding connective tissue, especially collagen formation in fibrotic responses (FIG. 2). In contrast, sorafenib had little or no effect on fibroplasia or collagen formation. In addition, nintedanib and lenvatinib significantly reduced alpha SMA (smooth muscle actin) staining by immunohistochemistry analysis. Alpha SMA is a key marker of myofibroblasts, whose function in wound healing and extracellular matrix formation is associated with fibrotic disease. Sorafenib, on the other hand, had no effect on alpha SMA relative to vehicle treatment (FIG. 2).

Study results show histological reduction in neovascularization, fibroplasia, collagen-related materials, and SMA by nintedanib and lenvatinib. Results from this study also show that not all multikinase inhibitors will be effective in treating fibrotic tissue responses. In particular, nintedanib and lenvatinib are effective, but sorafenib is not.

Example 2

In order to investigate the anti-scarring effect of topically applied test compounds following ocular surgeries, glaucoma filtration surgery was performed on rabbit eyes. Postoperative subconjunctival wound healing is a major cause of late bleb failure after glaucoma filtration surgery in humans. Select multikinase inhibitors were tested for effect on bleb survival over time. Inhibition of subconjunctival fibrosis following surgery will improve bleb survival. Vehicle was used as a negative control and pirfenidone was used a positive control.

A scleral tract was created in the left eyes superiorally by tunneling a beveled 22-gauge intravenous cannula through the sclera, beginning behind the limbus and continuing until the cannula is visible in the anterior chamber. The cannula was flushed with sodium heparin (1000 units) prior to placement. The cannula needle was withdrawn and the cannula advanced beyond the pupillary margin to prevent iris blockage of the tube. The cannula was trimmed approximately 2 mm and secured to the sclera using suture. Both the Tenon's and the conjunctiva were sutured with 9-0 Prolene. Six rabbits were used per group and the left eye of each rabbit underwent glaucoma filtration surgery. The treatment groups include vehicle as a negative control, pirfenidone (1%, w/w) as a positive control, sorafenib (0.3%, w/w), and lenvatinib (0.3%, w/w). Eyedrops (35 µL) were topically applied to the eyes following surgery three times a day for 30 days. All animals were sacrificed on Day 30.

Ophthalmic examinations showed a high total ocular examination score (based on a modified Hackett and McDonald ocular grading system) in the surgery eyes. Bleb was monitored throughout the study. Bleb volumes were measured with the use of calibrated calipers. Overall bleb volumes were uniformly increased at Day 2, with a large reduction of volume at Day 4. There were differences noted between groups at Day 7, and the majority of blebs were gone by Day 14 through Day 30, indicating bleb failure due to subconjunctival scarring. Results of the vehicle and pirfenidone groups were similar to those reported in the literature (Zhong H et al., Invest Ophthalmol Vis Sci, 52: 3136-3142, 2011). FIG. 3 shows a representative bleb on Day 4 in an eye treated with 0.3% sorafenib three times daily.

When the blebs were monitored over time, pirfenidone (the positive control) and lenvatinib treatments kept bleb survival on Day 7, as compared to the vehicle and sorafenib groups (FIG. 4).

On Day 14, all of the sorafenib treated eyes demonstrated bleb failure. On Day 30, all of the eyes treated with vehicle and pirfenidone demonstrated bleb failure, while the lenvatinib-treatment group still had bleb remaining (1 of 6 animals).

These results show that treatments with certain multikinase inhibitors, such as lenvatinib, but not sorafenib, are able to inhibit ocular fibrosis in models of subconjunctival scarring associated with ocular surgeries.

Example 3

The fact that not all multikinase inhibitors are effective in the treatment or prevention of ocular fibrosis suggests that effective compounds must interfere with multiple phases of the fibrosis. We suspect that TGF beta might be involved. Fibrosis is a late phase reactive and/or reparative response in tissues associated with disease, trauma, genetic disorders, or infection. There is a strong overlap in the pathophysiology of fibrosis regardless of the organ or tissue involved. Therefore, we used a more convenient dermal wound model to test whether TGF beta inhibition is needed.

Test compounds were examined in full-thickness dermal wounds in rabbits. Seven male New Zealand White rabbits, ranging in body weight from 3.03 to 3.40 kg were used in this study. Four wounds were placed on the ventral surface of both ears using an 8 mm skin punch biopsy. Nintedanib (1.0%, w/w), lenvatinib (1.0%, w/w), and sorafenib (1.0%, w/w) were administered by 0.05 mL intradermal or intralesional injections on days 15 and 29 following surgery. Animals were euthanized 14 days following the last administration of test agents. The trauma sites were harvested and divided in half. One half was preserved in formalin for histological examination, and the other half was frozen for TGF beta analysis.

Tissue H&E staining was evaluated semi-quantitatively for inflammation and neovascularization. Tissue fibrosis and collagen organization were evaluated by Mason's trichrome staining. Scores for four intradermal sites receiving test articles were averaged. Most scar tissues were composed of neovascularization, fibroblast hyperplasia, collagen disorganization and re-epithelialization.

Test compound nintedanib (Table 1) produced much less neovascularization and about the same fibrosis as untreated wounds. The average total score of the test wounds was 1.5 lower than untreated wounds. Overall, the test sites have less scar formation, as compared with the control sites.

TABLE 1

Histopathology Findings of Rabbit Ear Wound Treated with Intradermal Dosing of 1% w/w Nintedanib

| | Neovascularization | Fibrosis/Collagen | Re-epithialization | Total Score |
|---|---|---|---|---|
| Treated Mean | 1 | 3 | 0.5 | 4.5 |
| Untreated Control | 3 | 3 | 0 | 6 |

Test compound sorafenib (Table 2) produced slightly increased neovascularization and similar, or increased fibrosis, as compared to the control sites. Overall, the test compound does not appear to have reduced scar formation, as compared to the untreated wound sites.

TABLE 2

Histopathology Findings of Rabbit Ear Wound Treated
with Intradermal Dosing of 1% w/w Sorafenib

| | Neovas-cularization | Fibrosis/Collagen | Re-epithialization | Total Score |
|---|---|---|---|---|
| Treated Mean | 3 | 2.5 | 0.3 | 5.8 |
| Untreated Control | 2 | 2 | 0 | 4 |

Test compound lenvatinib (Table 3) appeared to produce decreased fibrosis, as compared to the control wound sites. The total score for the treated sites was 0.5 lower than the control wound.

TABLE 3

Histopathology Findings of Rabbit Ear Wound Treated
with Intradermal Dosing of 1% w/w Lenvatinib

| | Neovas-cularization | Fibrosis/Collagen | Re-epithialization | Total Score |
|---|---|---|---|---|
| Treated Mean | 2 | 2.5 | 0 | 4.5 |
| Vehicle Control | 2 | 3 | 0 | 5 |

TGF-β mRNA expression in the treated trauma samples was compared to the expression in the untreated samples, and the results are shown in FIG. 5. In general, the mean folds of TGF-β mRNA expression in the nintedanib and lenvatinib treated samples are lower than the expression level in the untreated trauma samples. In contrast, samples from animals treated with the multikinase inhibitor sorafenib did not show mean TGF-β expression levels significantly different from the untreated trauma samples. These results support our prediction that effective inhibitors of ocular fibrosis would suppress the expression of TGF-β.

These data support the fact that nintedanib and lenvatinib possess a certain spectrum of multikinase inhibitory activities necessary to treat ocular fibrosis associated with disease states, disorders and surgical procedures. The certain spectrum of multikinase inhibition involves the inhibition of the signaling pathway of TGF-β, among other things.

Example 4

The anti-fibrotic effects of test compounds were also evaluated in a subretinal fibrosis model in C57BL/6 mice. Three to five lesions were generated in the Bruch's membrane of the study eye using laser photocoagulation (75-μm spot size, 0.1-s duration, 90 mW, OcuLight TX 532 nm). Subretinal fibrosis started to form 5-7 days post laser application. Test compounds having certain spectrum of multikinase inhibition activities or vehicle were intravitreally injected on the day of laser application. The dosing concentration of the test compounds was 1% (w/w) of nintedanib and lenvatinib. The control groups were vehicle and mouse VEGF164 antibody. There were 12 mice per treatment group. Approximately, 1 μL each of the test compounds, vehicle, or positive control was injected intravitreally to the right eye of each animal. On Days 15 and 35, the eyes were examined with fluorescein angiography, followed by enucleation. Immunostaining on the dissected choroid was used to assess subretinal fibrosis (e.g., collagen 1, isolectin B4 and/or DAPI). The primary antibodies used were fluorescence conjugated isolectin B4 (FITC-conjugated isolectin B4) and anti-collagen type I antibody. Representative images of fluorescein fundus angiography, isolectin B4 and DAPI are shown in FIG. 6. Treatment of anti-VEGF did not have any notable effect on subretinal fibrosis, as compared to the vehicle treatment group. Both nintedanib and lenvatinib produced marked reductions in neovascular lesion sizes. Study results showed that lenvatinib and nintedanib have therapeutic effects in the treatment of subretinal fibrosis. Thus, these compounds can be used to treat subretinal fibrosis associated with proliferative retinal diseases.

Example 5

The objective of this ten-day study was to assess the local tolerance and ocular distribution of nintedanib and lenvatinib (0.3% w/w) when administered by topical ocular instillation in the eyes. Five to seven male New Zealand White rabbits were used per treatment group. Each eye received a 35 μL eyedrop of vehicle, nintedanib (0.3% w/w), or lenvatinib (0.3%) three times daily for 10 days. After the last dose on Day 11, the animals were sacrificed and eyes were enucleated, and plasma and the ocular tissues were collected. Tissue and plasma concentrations of these compounds were measured by LC-MS/MS.

The ocular tissue concentrations of these compounds in various tissues are listed in Tables 4 and 5. Topical instillation of 0.3% w/w nintedanib and lenvatinib delivered high drug concentrations to the anterior tissues of conjunctiva and cornea and significant concentrations in the choroid and retina of rabbits. As this level of drug exposure was maintained in the eyes, very slight to moderate conjunctival congestion and swelling were observed. The extents of these congestion and swelling were similar among the groups (including the vehicle control) over the course of the 10-day observation period.

TABLE 4

Ocular Tissue Concentration of Nintedanib and Its Metabolite
in ng/gm After Topical Instillation of 0.3% w/w Nintedanib
Three Times Daily for Ten Days in Rabbit Eyes.

| Nintedanib | Mean | SEM | N |
|---|---|---|---|
| Conjunctiva | 118.2 | 70.27 | 5 |
| Conj Met | 6.85 | 2.16 | 5 |
| Cornea | 36.17 | 9.27 | 5 |
| Cornea Met | 33.50 | 9.27 | 5 |
| Aqueous Humor | 0 | 0 | 5 |
| AqH Met | 1.7 | 0.3 | 5 |
| Iris Ciliary Body | 2.99 | 0.94 | 5 |
| ICB Met | 2.99 | 0.94 | 5 |
| Vitreous Humor | 0 | 0 | 5 |
| VH Met | 0 | 0 | 5 |
| Choroid | 10.00 | 3.86 | 5 |
| Choroid Met | 3.70 | 0.52 | 5 |
| Retina | 0.451 | 0.087 | 5 |
| Ret Met | 0 | 0 | 5 |

TABLE 5

Ocular Tissue Concentration of Lenvatinib in ng/gm
After Topical Instillation of 0.3% w/w Lenvatinib
Three Times Daily for Ten Days in Rabbit Eyes.

| Lenvatinib | Mean | SEM | N |
|---|---|---|---|
| Conjunctiva | 37.13 | 6.01 | 5 |
| Cornea | 52.37 | 4.12 | 6 |

TABLE 5-continued

Ocular Tissue Concentration of Lenvatinib in ng/gm
After Topical Instillation of 0.3% w/w Lenvatinib
Three Times Daily for Ten Days in Rabbit Eyes.

| Lenvatinib | Mean | SEM | N |
| --- | --- | --- | --- |
| Aqueous Humor | 1.3 | 0.2 | 6 |
| Iris Ciliary Body | 12.72 | 1.55 | 6 |
| Vitreous Humor | 0 | 0 | 6 |
| Choroid | 18.47 | 4.31 | 6 |
| Retina | 8.72 | 0.80 | 6 |

The plasma concentration, mean (±SD), on Day 11 for nintedanib was below the quantifiable limit, for its metabolite was 1.09 (±0.14) ng/mL, and for lenvatinib was 98.5 (±11) ng/mL.

Example 7. Distribution in Ocular Tissue after Topical Instillation of Sorafenib and Lenvatinib as Ophthalmic Eyedrop in Rabbit Eyes The objective of this study was to assess the local tolerance and ocular distribution of sorafenib and lenvatinib (0.3% w/w) when administered by topical ocular instillation in the eyes. Five to six male New Zealand White rabbits were used per treatment group. Each right eye received a 35 μL eyedrop of the vehicle, sorafenib (0.3% w/w), or lenvatinib (0.3% w/w) three times daily for 5 days. On Dosing Day 5, the animals were sacrificed and eyes were enucleated, and plasma and the ocular tissues were collected. Tissue and plasma concentrations of the compounds were measured by LC-MS/MS.

Animals among the study groups displayed normal body weight gains over the course of the study. Ocular examinations of the right eye did not show significant findings. Average overall examination scores of all animals in all groups were close to the baseline values for the duration of the study. Intraocular pressure (IOP) was measured using a Tonovet probe. Six consecutive measurements were obtained and the average IOP shown on the display was recorded. IOPs in the right eye remained near to slightly above the baseline values for the duration of the experiment in all groups.

The ocular tissue concentrations for these drugs are listed in Tables 6 and 7. Topical instillation of 0.3% w/w sorafenib and lenvatinib delivered high drug concentrations to the anterior tissues of conjunctiva, sclera and cornea and significant concentrations in the choroid and retina of rabbits.

TABLE 6

Ocular Tissue Concentration of Sorafenib in ng/gm
After Topical Instillation of 0.3% Sorafenib Three
Times Daily for Five Days in Rabbit Eyes.

| Sorafenib | Mean | SEM | N |
| --- | --- | --- | --- |
| Conjunctiva | 859.8 | 528.9 | 6 |
| Cornea | 131.4 | 10.0 | 6 |
| Sclera | 16.36 | 4.00 | 6 |
| Aqueous Humor | 0 | 0 | 6 |
| Iris Ciliary Body | 3.337 | 0.408 | 6 |
| Vitreous Humor | 0.11 | 0.08 | 6 |
| Retina | 17.36 | 2.41 | 6 |
| Choroid | 8.191 | 0.702 | 6 |

TABLE 7

Ocular Tissue Concentration of Lenvatinib in ng/gm
After Topical Instillation of 0.3% Lenvatinib Three
Times Daily for Five Days in Rabbit Eyes.

| Lenvatinib | Mean | SEM | N |
| --- | --- | --- | --- |
| Conjunctiva | 299.7 | 141.9 | 6 |
| Cornea | 178.0 | 41.2 | 6 |
| Sclera | 49.05 | 7.11 | 6 |
| Aqueous Humor | 5.49 | 1.14 | 6 |
| Iris Ciliary Body | 18.24 | 2.04 | 6 |
| Vitreous Humor | 0.619 | 0.09 | 6 |
| Retina | 23.53 | 2.91 | 6 |
| Choroid | 38.00 | 3.66 | 6 |

The plasma concentrations, mean (±SD), on Day 5 of dosing were 5.09 (±1.27) ng/mL for sorafenib, and 131 (±24) ng/mL for lenvatinib.

The concentrations of both sorafenib and lenvatinib in anterior segment tissues, including conjunctiva and cornea, were high and essentially equal. These results support the conclusion that any differences in animal efficacy model by topical administration to eyes are due to differences in their pharmacological activity and not to their pharmacokinetic profiles.

The above examples show that ophthalmic applications of compounds of the invention can achieve sufficient concentrations to result in therapeutic effects.

While embodiments of the invention have been illustrated with a limited number of examples, one skilled in the art would appreciate that other modifications and variations are possible without departing from the scope of the invention. Therefore, the scope of protection of the invention should only be limited by the attached claims.

What is claimed is:

1. A method for treating fibrosis associated with an eye-related disease or disorder, comprising: administering an effective amount of a pharmaceutical composition of lenvatinib or a salt thereof to a subject in need thereof, wherein the subject is suffering from macular degeneration that has associated fibrosis, wherein lenvatinib is administered topically, by intraocular injection, by intravitreal injection, by intra-lesional injection, by subconjunctival injection, by sub-tenon injection, or by intra-canalicular delivery, and wherein lenvatinib is the only active component in the composition.

2. The method of claim 1, wherein the pharmaceutical composition is administered topically to an eye of the subject.

3. The method of claim 1, wherein the pharmaceutical composition is administered to the subject by intraocular injection.

4. The method of claim 1, wherein the pharmaceutical composition is administered to the subject by intravitreal injection.

5. The method of claim 1, wherein the pharmaceutical composition is administered to the subject by intra-lesional injection.

6. The method of claim 1, wherein the pharmaceutical composition is administered to the subject by subconjunctival injection.

7. The method of claim 1, wherein the pharmaceutical composition is administered to the subject by sub-tenon injection.

8. The method of claim 1, wherein the pharmaceutical composition is administered to the subject by intra-canalicular delivery.

9. A method for treating fibrosis associated with an eye-related disease or disorder, comprising: administering an effective amount of a pharmaceutical composition of lenvatinib or a salt thereof to a subject in need thereof, wherein the pharmaceutical composition contains 0.3% (w/w) to 1% (w/w) lenvatinib, administered topically, by intraocular injection, by intravitreal injection, by intra-lesional injection, by subconjunctival injection, by sub-tenon injection, or by intra-canalicular delivery, and wherein lenvatinib is the only active component in the composition.

10. The method according to claim 9, wherein the eye-related disease or disorder is compromised corneal transparency, corneal scar formation, secondary cataract formation, glaucoma filtration surgery, ocular surgical procedures and implants, photorefractive keratectomy, laser in situ keratomileusis, formation and contraction of pre- and epiretinal membranes, proliferative vitreoretinopathy, proliferative diabetic retinopathy, diabetic macular edema, subretinal fibrosis/scarring, retinal gliosis, and formation of choroidal membranes, age-related macular degeneration, or retinal vein occlusion.

11. The method according to claim 9, wherein the eye-related disease or disorder is macular degeneration.

12. The method of claim 9, wherein the pharmaceutical composition is administered topically to an eye of the subject.

13. The method of claim 9, wherein the pharmaceutical composition is administered to the subject by intraocular injection.

14. The method of claim 9, wherein the pharmaceutical composition is administered to the subject by intravitreal injection.

15. The method of claim 9, wherein the pharmaceutical composition is administered to the subject by intra-lesional injection.

16. The method of claim 9, wherein the pharmaceutical composition is administered to the subject by subconjunctival injection.

17. The method of claim 9, wherein the pharmaceutical composition is administered to the subject by sub-tenon injection.

18. The method of claim 9, wherein the pharmaceutical composition is administered to the subject by intra-canalicular delivery.

* * * * *